Figure 1:
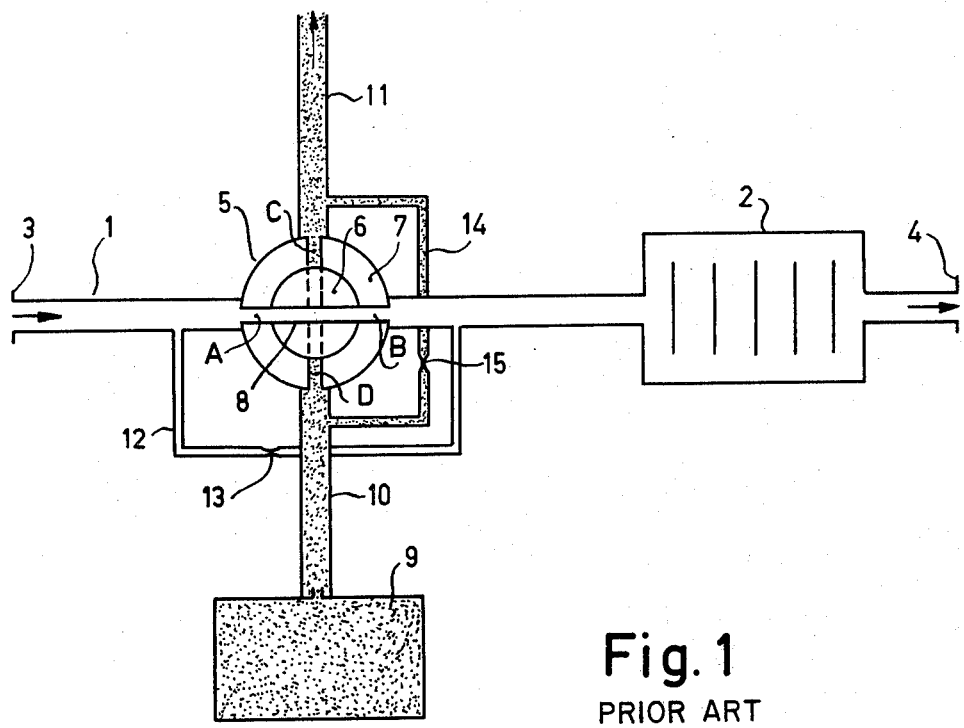

United States Patent [19]
Kruishoop

[11] 3,998,239
[45] Dec. 21, 1976

[54] GAS DOSING ARRANGEMENT
[75] Inventor: Johan Christiaan Willem Kruishoop, Eindhoven, Netherlands
[73] Assignee: U.S. Philips Corporation, New York, N.Y.
[22] Filed: May 30, 1974
[21] Appl. No.: 474,809
[30] Foreign Application Priority Data
June 1, 1973  Netherlands ............... 7307629
[52] U.S. Cl. .................. 137/101.11; 137/564.5; 222/190; 222/194
[51] Int. Cl.² ................... G05D 11/035
[58] Field of Search ............ 137/101.11, 101.31, 137/564.5; 222/3, 190, 194; 73/421.5 R, 422 TC

[56] References Cited
UNITED STATES PATENTS

| | | | |
|---|---|---|---|
| 2,033,427 | 3/1936 | Guilford | 137/564.5 |
| 2,618,510 | 11/1952 | Mills | 137/564.5 |
| 3,109,452 | 11/1963 | Hicks | 137/564.5 |
| 3,227,312 | 1/1966 | Solvik et al. | 222/194 X |
| 3,590,846 | 7/1971 | Eisele et al. | 137/101.11 |
| 3,799,396 | 3/1974 | Ashmead et al. | 137/101.11 X |

FOREIGN PATENTS OR APPLICATIONS 340,276  9/1921  Germany ............ 137/101.11

Primary Examiner—Robert G. Nilson
Attorney, Agent, or Firm—Frank R. Trifari; Ronald L. Drumheller

[57] ABSTRACT

An arrangement for dosing gas into a flow line comprising a storage vessel divided into two compartments by a movable gas-tight wall, the first compartment being connected directly to the flow line and the second compartment, which holds the dose gas, being connected to the flow line further downstream through a periodically switching metering valve, across which at least a slight pressure drop is maintained.

15 Claims, 6 Drawing Figures

GAS DOSING ARRANGEMENT

The invention relates to a gas dosing arrangement which comprises a flow line for a carrier gas including a mixing vessel and an upstream periodically switching gas metering valve for supplying pulses of dosing gas from a storage vessel to the carrier gas.

Gas dosing arrangements are employed in respiration apparatus for patients, in which apparatus a controlled quantity of dosing gas is to be added to a controlled air stream, and they are employed in gas-analysis equipment, which equipment can be calibrated by adding a known amount of calibration gas to a carrier gas and measuring the concentration of said calibration gas with the equipment.

For mixing the dosing gas with the carrier gas it is necessary that the flow of both gases be measured and controlled with sufficient accuracy. For very high flow rates of the carrier gas this can be realized very simply, even in case of substantial dilution in the p.p.m. range, $10^{-6}$, or in the p.p.b. range ($10^{-9}$). For small doses and low flow rates, however, special provisions are necessary.

It is obvious that a small quantity of the dosing gas may be mixed with a very large quantity of the carrier gas, but a substantial part of the mixture is generally unused and must be discharged. This dilution and discharging may also be effected in several stages. A drawback of this method is that expensive provisions are required when preparing mixtures with expensive or poisonous dosing gases which may not readily be discharged, or when the carrier gas must be prepared with care, and then a substantial part is not used. Sometimes, dilution is possible by bleeding off a part of the previously dosed carrier gas stream, extracting dosing gas from said stream, and subsequently adding the purified gas again. In this case there is also a loss of dosing gas and additional provisions for filtering are necessary.

Known and generally applicable methods of measuring and controlling a very small dosing stream in a carrier gas stream of given magnitude are:

1. Permeation

The dosing gas is contained in a vessel having a wall consisting of an elastomer, such as silicone rubber or polythene, along which the carrier gas flows. Through permeation a constant output of dosing gas is obtained of very low value. The output is determined by the nature and the dimensions of the elastomer layer, by the nature and pressure of the dosing gas, by the temperature and sometimes by the relative humidity. A disadvantage in this respect is that the output of the dosing gas cannot be stopped or changed in a simple and rapidly measurable manner. Furthermore each source of dosing gas must be calibrated separately in view of the poor reproducibility of the elastomers, dependence on the said other factors, and the output decrease due to the decrease in pressure within the vessel as it gradually becomes empty.

2. Mechanical methods

With these methods the dosing gas flows from a storage vessel under the influence of a difference in pressure, which may be controllable via a controllable flow resistance or valve, in the line through which the carrier gas flows and in which moreover mixing takes place. Usually, the dosage can be measured and controlled satisfactorily, and stopped, if necessary. For small dosing streams, however, expensive and vulnerable mechanical provisions are needed.

Known mechanical methods include a storage vessel holding pressurized dosing gas and an adjustable flow controller and perhaps a flow meter capable of delivering dosing gas streams as small as 0.1 millilitre per minute. Another known mechanical method is the injection syringe having a cylinder of dosing gas closed at one end by a plunger that may be uniformly moved by a motor and closed at the other end by a dosing needle with a very narrow opening. This allows dosing rates as low as some microlitres per minute. A disadvantage of said methods is the high sensitivity to variations in exterior pressure or temperature.

A better method of obtaining an accurate and properly adjustable gas dosage is the pulsing method, in which a valve is opened periodically to inject a relatively large dosing gas stream into a carrier gas stream for a short time. However, a device such as a mixing vessel must be provided so as to obtain homogenization.

Another example of said pulsing method is described in the article by Breuer and Schreckling "Eine Anordnung zur kontinuierlichen Erzeugung genauer Gasspurenkonzentrationen fur die Uberprufung anylytischer Verfahren" in A.T.M. (Archiv fur technisches Messen), Blatt V 723-34, January 1970, pages 5–10. By injecting at variable regular intervals a known quantity of dosing gas into the carrier gas stream and subsequent homogenization thereof in a mixing vessel, a concentration is obtained which is proportional to the injection rate. A drawback of this method is that the dosing gas must continuously flow, which means a high consumption of said gas. It is also not possible to obtain concentrations smaller than one p.p.m. without dilution, i.e. without loss of gases.

A gas dosing arrangement according to the invention eliminates said drawbacks and is characterized in that the flow line includes a first branch connected to a periodically switching gas metering valve which is connected to a storage vessel and a dosing compartment. The switching valve has at least a dosing position in which the flow line is connected to the dosing compartment and a filling position in which the dosing compartment is connected to the storage vessel. Furthermore, the storage vessel comprises two compartments, which are separated from each other by a movable gas-tight wall the first of which is connected to the flow line upstream of the first branch the second of which contains the dosing gas and is connected to the switching valve. The volume of the second compartment is many times greater than the volume of the dosing compartment in which a pressure difference prevails relative to the first compartment.

This arrangement is advantageous in that a fully closed gas dosing system is obtained which has no connection with ambient pressure and operates instead at a pressure which is related to the gas pressure which prevails in the flow line. In such an arrangement the entire supply of dosing gas is used for dosing, so that no unused dosing gas must be discharged as in the known dilution methods. Moreover, the parameters which determine the concentration, can be selected and set accurately.

By means of a dosing arrangement according to the invention it is possible to achieve a minimum concentration as low as one p.p.b at a flow rate for the carrier gas as low as 10 millilitres per minute, with an adjustment accuracy of one percent and a dynamic range of one thousand.

An advantageous application may be found in air pollution measuring equipment that must be calibrated at regular intervals. The dosing arrangement according to the invention complies with imposed standards to be imposed thereon, regarding miniaturization, automation, controllability, remote measurability, both analog and digital, and prolonged operation without maintenance, replacement or replenishing. Said properties also render the dosing arrangement extremely suited for application in laboratories.

Another advantage of the fully closed dosing system for measuring stations is that no diluted or undiluted streams of calibration gas are discharged into the atmosphere where they may affect the measurement of air pollutants. Owing to the slight consumption of dosing gas and carrier gas, a dosing arrangement according to the invention leads to economies in filters, measuring cells and storage of calibration gas so that a smaller and cheaper unit is obtained which can operate for a prolonged time without surveillance and maintenance.

In one embodiment the storage vessel is cylindrical and the movable wall is a plunger, which is sealed by a ring of mercury so that the wall is movable without friction and provides a hermetic seal for the dosing gas. Moreover, a visual indication of the residual amount of dosing gas may be obtained by monitoring the piston position. The weight of the plunger, with or without additional mass, provides an independent overpressure dp when the cylinder is disposed vertically. If the cylinder is made of a transparent material, such as glass, visual inspection of consumption is possible. A volume measurement per dose can be obtained in a simple manner by determining the volume between two plunger positions and dividing this by the number of doses required to move from one plunger position to the other.

For the movable wall it is also possible to use a bellows construction or a plastic foil.

To dose greater amounts, the dosing compartment in a preferred embodiment may be a capillary tube, in which a drop of liquid such as mercury can move. By including flow resistances in the flow lines, the drop can be moved by the resulting pressure differences, the capillary tube being filled with dosing gas when the switching valve is in the filling position and emptied when the switching valve is in the dosing position.

For small concentrations the contents of the switching valve, preferably a magnetically controllable valve, suffices as the dosing compartment. Thus, dosing volumes of a few microlitres can be obtained.

In a different embodiment of the gas dosing arrangement according to the invention the dosing gas supply line to the flow line may take the form of a narrow capillary tube which represents a high flow resistance. By controlling the dosing time Td and the difference in pressure dp, pressure and temperature independent dosing of small amounts is possible. It is then even possible to connect the dosing compartment permanently to the storage vessel.

It is to be noted that the gas dosing arrangement according to the invention may be used for all kinds of dosing gases and mixtures of gases which are stable and which do not affect the materials chosen. For example ozone and nitrogen dioxide may not be dosed using a mercury seal because they both affect mercury.

Figure 2:
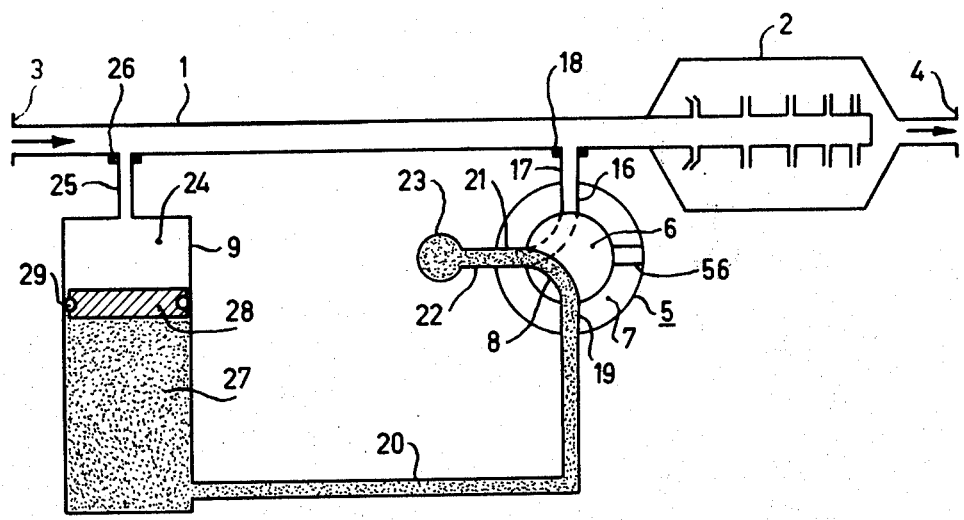
Figure 3:
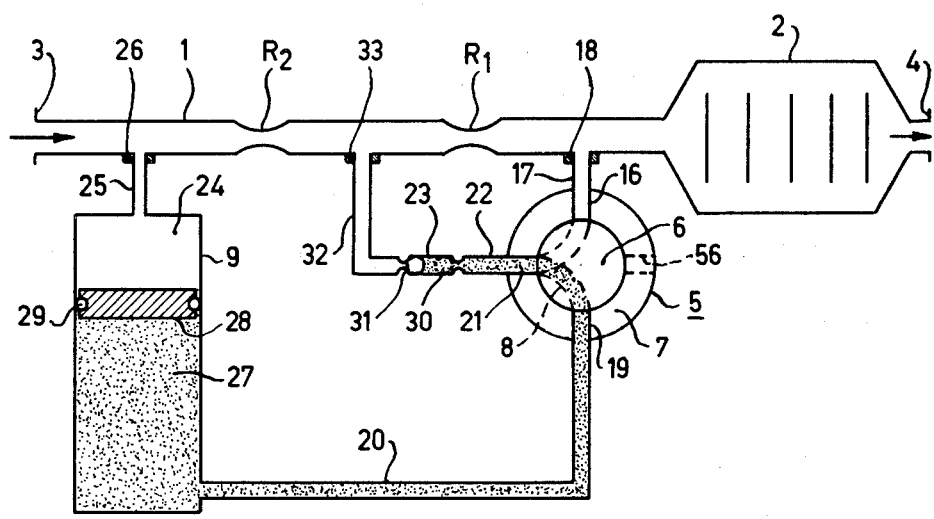
Figure 4:
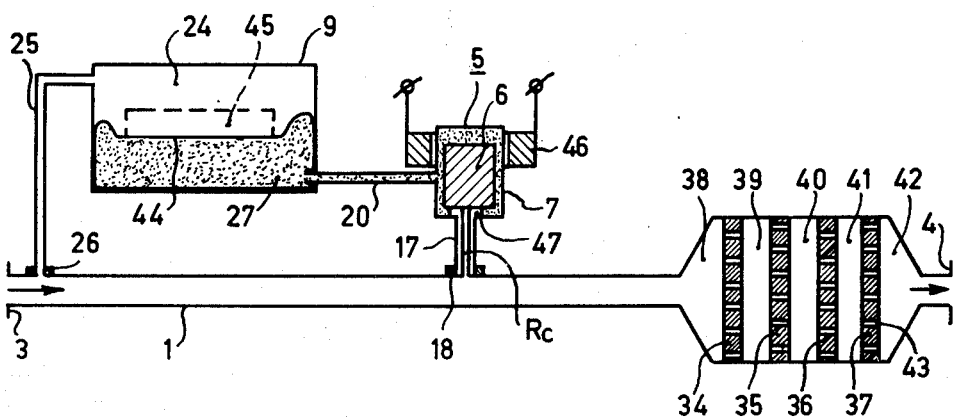
Figure 5:
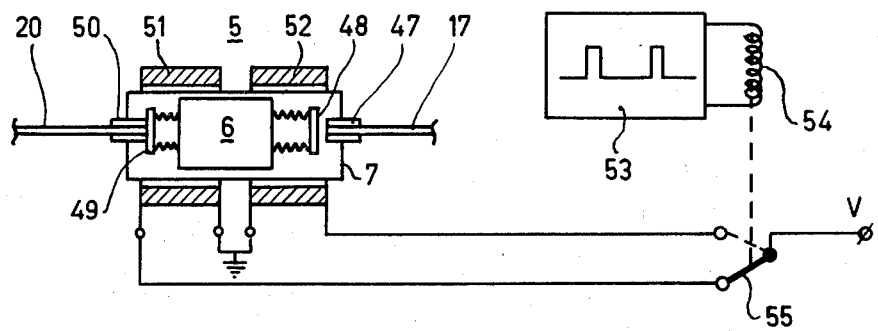
Figure 6:
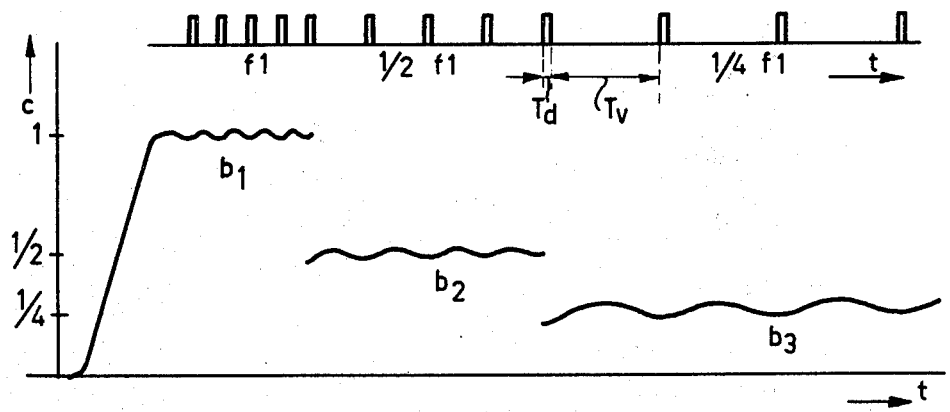

The invention will be described in more detail with reference to the drawing, in which FIG. 1 shows a known gas dosing arrangement, FIG. 2 shows a gas dosing arrangement according to the invention, FIG. 3 is an embodiment of the dosing arrangement according to the invention, FIG. 4 is a different embodiment according to the invention, FIG. 5 is an embodiment of a switching valve to be employed in a dosing arrangement according to the invention, and FIG. 6 shows a diagram of the control pulses and the concentrations obtained plotted against time.

FIG. 1 schematically shows a known gas dosing arrangement, the means by which the gas streams are obtained and their flow rates measured not being shown. In a flow line 1, which is provided with a mixing vessel 2 a stream of a carrier gas is sustained which enters at an inlet 3 and leaves the line at an outlet 4. The line 1 includes a periodically switching gas metering valve 5, which is represented as a rotary cock with a housing 7 and a rotatable interior member 6, provided with a bore 8. In the shown position of the interior member 6, the bores A and B in the housing are interconnected through the bore 8 and the carrier gas for the most part flows directly from the inlet 3 to the outlet 4. In the other position, shown by dotted lines and turned 90°, the bore 8 interconnects the bores C and D in the housing 7 and a dosing gas from a storage vessel 9 may flow via a line 10 to a discharge line 11. In the meantime the carrier gas flows via a bleeding line 12 with a restriction 13. The bore 8 is now filled with an amount of dosing gas which is determined by the volume of the bore 8 and the pressure of the dosing gas.

Said amount of dosing gas in the bore 8 is subsequently carried along by the carrier gas when the cock is reset to the original position. In the vessel 2 mixing takes place. By suitably dimensioning said vessel and selecting the frequency of rotation f of the cock it is possible, despite the pulsatory dosing, to obtain at the outlet 4 an adjustable concentration of dosing gas relative to the carrier gas, which at a low frequency $f$ exhibits a slight ripple (of the frequency $f$). In the position A-B of the cock the dosing gas flows from the line 10 to line 11 via the bleeding line 14 with restriction 15.

FIG. 2 schematically shows a dosing arrangement according to the invention, the same reference numerals being used for corresponding parts of FIG. 1.

The switching valve 5 is not included in the line 1. The housing 7 is provided with a bore 16, to which a first line 17 is connected, which is connected to a first branch 18 of the flow line 1. A bore 19 is connected to the vessel 9 by a second line 20 and a bore 21 is connected to a dosing compartment 23 by a third line 22. In a filling position of the switching valve (shown), the bore 8 of the interior member 6 connects the line 20 to the line 22 and in a 90° rotated dosing position (shown by dotted lines), the line 22 is connected to the line 17. The storage vessel 9 is divided into a first compartment 24, which by a fourth line 25 is connected to a second branch 26 in the flow line 1, and a second compartment 27 which is connected to the line 20 and which contains the dosing gas. The two compartments are separated by a gas-tight movable wall, which in this case takes the form of a plunger 28 which can reciprocate loosely and thus without friction in the vessel 9. For satisfactory gas-tight sealing a mercury ring 29 is provided in a recess at the circumference of the plunger 28. By dividing the area O of the plunger by the weight G of the plunger, it is possible to determine the overpressure dp of the dosing gas in the compartment 27 relative to the pressure which prevails in the compartment 24 and which equals the pressure in the flow line 1. In the filling position of the valve 5 the dosing compartment 23 with a volume Vd communicates with the compartment 27 of the vessel 9, so that the pressure in the volume Vd is $p+dp$, where p is the pressure in the line 1. When the valve 5 is now set to the dosing position, the compartment 23 communicates with the flow line and a part of the dosing gas in the compartment 23 will flow into the line 1 owing to the difference in pressure dp. When the entire difference in pressure dp is eliminated because the dosing time Dt, during which the dosing position is assumed, is sufficiently long, it is possible to calculate the volume Vc of dosing gas injected into the carrier gas, namely:

$$Vc = (dp/p)Vd \qquad (1)$$

FIG. 3 shows the dosing arrangement of FIG. 2 with a special embodiment of the dosing compartment. Said compartment now consists of a capillary tube with dosing compartment 23, in which a drop of mercury can assume an extreme position 30 (dotted) and another extreme position 31 (shown). One end of the capillary tube is connected to the line 22 and the other end via a line 32 to a third branch 33 in the flow line 1. FIG. 3 also shows that the overpressure dp may be adjusted by means of a restriction R2 in the flow line 1, located between the branches 26 and 33. Thus, the overpressure is related to the flow rate F1 of the carrier gas, so that:

$$dp = F1.R2 + G/o \qquad (2)$$

In the filling position of valve 5 the overpressure dp causes the drop of mercury to move from position 30 to position 31, so that the dosing compartment 23 is filled with dosing gas. In order to return the drop of mercury, so that the entire gas content of the dosing compartment is injected, a restriction R1 is included between the branches 18 and 33 in the line 1. In this case the dosing volume Vc is determined by:

$$Vc = (1+dp/p)Vd \qquad (3)$$

FIG. 4 shows the dosing arrangement with some special embodiments of components.

The mixing vessel 2 takes the form of a multiple exponential diluter. For this purpose it is divided into several mixing chambers 38–42 by means of perforated partitions 34–37. The gas can flow from one mixing chamber to the other through a multiplicity of long and thin ducts 43 in the thick-walled partitions 34–37. Mixing in the mixing chambers 39–42 is substantially effected by diffusion. For this purpose said mixing chambers have a small dimension in the flow direction of the gas and have a large cross-section in a direction perpendicular thereto, so that the diffusion path in the flow direction and the linear flow rate are very small. In order to ensure that the diffusion path perpendicular to the direction of flow is small, the mixing chambers communicate through a multiplicity of narrow perforations or ducts 43 in the thick walled partitions 34–37, which are uniformly distributed over the entire cross-section of the partitions. Mixing, moreover, is promoted by the higher flow rates and the resultant convection near the inlet and outlet of each perforation.

The storage vessel 9 has a compartment 27 which is bounded by a flexible material 44 acting as a movable gas-tight wall. If desired, a weight 45 can provide the pressure difference dp.

The periodically switching gas metering valve 5 in this case is of the fully enclosed type and is magnetically controllable. The housing 7 has a connection for the line 20 and a connection for the line 17. Inside the housing 7 a plunger is movable from the filling position to the dosing position under the influence of a spring force and the magnetic forces produced by a coil 46 disposed outside the housing 7. Plunger 6 is of a magnetic material and the housing 7 of a non-magnetic material.

The remaining volume within the casing serves as the dosing compartment and is permanently connected to the storage vessel 9. The line 17 takes the form of a narrow capillary with a flow resistance Rc. When the coil 46 is energized the plunger 6 moves upwards and thus comes clear of the seating 47, which so far was in gas-tight engagement with the plunger.

Owing to the difference in pressure dp and the flow resistance Rc a dosing-gas flow is obtained of constant value. While in this dosing position, the dosing time Td now also determines the volume of dosing gas which is injected into the line 1. Consequently, the dosing volume Vc may be said to satisfy the relationship:

$$Vc = dpTd/Rc \qquad (4)$$

FIG. 5 schematically shows a switching valve with control system, which is of the same type as the magnetic valve of FIG. 4.

The plunger 6 is provided with a resilient seal 48, which cooperate with the seating 47, to which the line 17 is attached, and is provided with a resilient seal 49, which cooperates with the seating 50, to which the line 20 is attached. Outside the non-magnetic housing 7 two coils 51 and 52 are provided for the operation of the plunger 6. If neither of the two coils is energized the plunger 6 is the middle of the housing and the seals 48 and 49 close the seatings 47 and 50. When coil 51 is energized the plunger 6 moves in the direction of said coil and seal 48 comes clear of the seating 47, so that the dosing compartment of the housing then communicates with line 17. Upon energization of the coil 52 the dosing compartment communicates with line 20. Naturally, one of the coils may be replaced by a mechanical spring, which always presses the plunger against one of the seatings. A switch 55 in FIG. 5 controls the coils 51 and 52 from a power supply V. The switch 55 may be a relay with a coil 54, which can be energized by an adjustable pulse source 53. The dose can be adjusted by selection of the pulse durations as is indicated in FIG. 6.

In FIG. 6 a pulse train is shown in which the time Td is constant and in which the time Tv may vary. When said times represent the dosing time and the filling time respectively, the dose rate f will be determined by $f = 1/(Td + Tv)$. The graph under the pulse train plots the concentration C of the resulting mixture as a function of time corresponding approximately with as that of the pulse train). At $b1$ a concentration 1 corresponds with a frequency f1. When the frequency changes to ½f1, the concentration at $b2$ also becomes ½. Similarly, the average concentration is ¼ at $b3$ for a frequency ¼f1.

The ripple in graphs b1, b2, b3 has been exaggerated to indicate that the gas dosing system is in principle digital. For example, an exponential diluter, as denoted by the reference numeral 2 in FIG. 4, may be designed so that at a flow rate of the carrier gas of 2.5 millilitres per second and a rate of $10^{-2}$ dose per second, i.e. 1 every 100 seconds, the rise and fall times of the vessel are 300 seconds and the ripple is only 5%.

Depending on the desired dose the dosing time Td may be $10^{-1}$ to $10^{-2}$ seconds, and the flow rate of the carrier gas 0.2 to 3 millilitres per second.

When the volumes Vc, as in the equations (1), (3) and (4), are multiplied by the dose rate f, a flow rate of the dosing gas is obtained. By dividing said flow by the carrier gas flow rate F1, the concentration C can be calculated. For a system, as described with reference to FIG. 4, using the equation (4) the concentration may be expressed in parts by volume:

$$C = \frac{f \cdot dp \cdot Td}{Rc \cdot F1}$$

It is evident that the various embodiments, as shown in FIGS. 2 3, 4 and 5 of the mixing vessel 2, the storage vessel 9, the switching valve 5, the dosing compartment 23 and the line 17 are not limited to the combinations shown in the Figures. Depending on the application a suitable combination must be selected.

The switching cock 5, as shown in FIGS. 2 and 3, may have more positions than the dosing and filling position. For example, if a bore 56 is provided in the housing 7 opposite the bore 21, a connection with bore 19 may be established for filling the storage vessel 9 with dosing gas. A connection between bore 56 and bore 16 may be of interest for feeding in gases to be measured. In such a case a measuring cell will be connected to the outlet 4 and a cleaning filter to inlet 3. The gas to be measured flows either directly to the measuring cell via connection 16-56, or is purified via the filter and fed through line 1 while the cock is in position 19-21. In this position the dosing compartment may also be filled with a known amount of the components to be measured for calibration purposes. The cock is then moved to position 21-16 for calibration.

What is claimed is:

1. Gas dosing apparatus for metering a dose gas into a carrier gas stream, comprising:
   a flow line for connecting an inlet for carrier gas to an outlet, said flow line having first and second branches respectively downstream and upstream relative to each other and means downstream of said branches for homogenizing a gas stream;
   a gas storage vessel having a movable gas-tight wall dividing said storage vessel into a first compartment connected to said second branch and a second compartment for holding dose gas;
   means for maintaining a pressure difference between dose gas held in said second compartment and carrier gas at said first branch;
   a gas metering valve having a dosing compartment associated therewith, said valve being periodically switchable between a filling position in which said dosing compartment is in open communication with only said second compartment receiving therefrom each time a fixed amount of dosing gas as the pressure in said dosing compartment increases to the pressure of said second compartment and a dosing position in which said dosing compartment is in open communication with only said first branch releasing thereto each time said fixed amount of dosing gas as the pressure in said dosing compartment decreases to the pressure of said first branch; and
   means for periodically switching said valve between said filling and dosing positions.

2. Gas dosing apparatus as claimed in claim 1 wherein said means for maintaining a pressure difference comprises means for exerting against said movable gas-tight wall a constant force in addition to the forces exerted by the gases in said first and second compartments.

3. Gas dosing apparatus as claimed in claim 2 wherein said means for exerting a constant force comprises a mass acted upon by gravity.

4. Gas dosing apparatus as claimed in claim 3 wherein said mass is the mass of said movable gas-tight wall.

5. Gas dosing apparatus as claimed in claim 1 wherein said gas storage vessel is cylindrical and said movable gas-tight wall comprises a plunger having a mercury ring for gas-tight sealing.

6. Gas dosing apparatus as claimed in claim 5 wherein the axis of said cylindrical storage vessel is vertically positioned with said second compartment under said plunger, said means for maintaining a pressure difference comprising the weight of said plunger pressed down by gravity against the dose gas in said second compartment thereby maintaining a higher pressure in said second compartment than in said first compartment.

7. Gas dosing apparatus as claimed in claim 1, wherein said means for maintaining a pressure difference comprises a flow restriction.

8. Gas dosing apparatus as claimed in claim 7 wherein said flow restriction is located in said flow line between said first and second branches.

9. Gas dosing apparatus as claimed in claim 1 wherein said movable gas-tight wall substantially surrounds said second compartment and is composed of a thin flexible material.

10. Gas dosing apparatus as defined in claim 1 wherein said dosing compartment is a capillary tube having a gas-sealing drop of liquid movable from one position to another, one end of said capillary tube communicating via said valve with said first branch and said second compartment when said valve is in said dosing and filling positions respectively and the other end of said capillary tube communicating with said flow line at a point between said first and second branches.

11. Gas dosing apparatus as defined in claim 10 and further comprising a flow restriction in said flow line between said first branch and said point where said capillary tube communicates with said flow line.

12. Gas dosing apparatus as defined in claim 11 and further comprising a second flow restriction in said flow line between said second branch and said point where said capillary tube communicates with said flow line.

13. Gas dosing apparatus as defined in claim 1 wherein the interior volume of said valve constitutes said dosing compartment.

14. Gas dosing apparatus as defined in claim 1 wherein said periodically switchable gas metering valve comprises a housing having a first opening connected to said first branch and a econd opening connected to said second compartment, and a plunger positionable in a filling position where said plunger blocks only said first opening and in a dosing position where said plunger blocks only said second opening.

15. Gas dosing apparatus as defined in claim 14 wherein said plunger is positionable in said filling or dosing positions by a magnetic field generated outside said housing.

* * * * *